(12) United States Patent
Feeney

(10) Patent No.: US 12,343,163 B2
(45) Date of Patent: Jul. 1, 2025

(54) IMAGING SYSTEM AND METHOD FOR ENHANCED VISUALIZATION OF NEAR SURFACE VASCULAR STRUCTURES

(71) Applicant: Michael Feeney, Wrentham, MA (US)

(72) Inventor: Michael Feeney, Wrentham, MA (US)

( * ) Notice: Subject to any disclaimer, the term of this patent is extended or adjusted under 35 U.S.C. 154(b) by 821 days.

(21) Appl. No.: 17/404,755

(22) Filed: Aug. 17, 2021

(65) Prior Publication Data

US 2021/0393194 A1    Dec. 23, 2021

Related U.S. Application Data

(63) Continuation-in-part of application No. 16/059,728, filed on Aug. 9, 2018, now abandoned.

(51) Int. Cl.
*A61B 5/00* (2006.01)
*G06T 7/00* (2017.01)

(52) U.S. Cl.
CPC ............ *A61B 5/489* (2013.01); *A61B 5/0077* (2013.01); *A61B 5/742* (2013.01); *G06T 7/0012* (2013.01); *G06T 2207/30101* (2013.01)

(58) Field of Classification Search
None
See application file for complete search history.

(56) References Cited

U.S. PATENT DOCUMENTS

| | | | |
|---|---|---|---|
| 5,847,394 A | 12/1998 | Alfano | |
| 5,929,443 A | 7/1999 | Alfano | |
| 8,586,924 B2 | 11/2013 | Demos | |
| 10,390,709 B2 | 8/2019 | Demos | |
| 10,939,869 B2 | 3/2021 | Demos | |
| 2012/0028944 A1 | 2/2012 | Loftsson | |
| 2018/0310872 A1* | 11/2018 | Tseng | A61B 5/14558 |
| 2019/0046108 A1* | 2/2019 | Feeney | A61B 5/7425 |
| 2019/0125258 A1* | 5/2019 | Miller | A61Q 17/04 |

* cited by examiner

*Primary Examiner* — Shahdeep Mohammed
(74) *Attorney, Agent, or Firm* — Lambert Shortell & Connaughton; David J. Connaughton, Jr.; Justin P. Tinger

(57) ABSTRACT

The present disclosure solves many problems. The main problem solved by the present disclosure is the problem of showing veins for patients whose veins may be hard to find. The present disclosure will greatly improve the venipuncture experiences for millions of people every day. The present invention discloses a system and method imaging objects in or behind a turbid medium comprising a light source adapted to illuminate an imaged area, an imaging device arranged to optically capture and relay an image, an electronic display to receive and display the image, and a control unit to control at least one spectral and polarization properties of the light source. Also disclosed is a camera module within an embodiment of the imaging device that provides for an alternative operation of the imaging device, without a control unit, and relaying of the image to the electronic display, which may be a tablet.

18 Claims, 13 Drawing Sheets

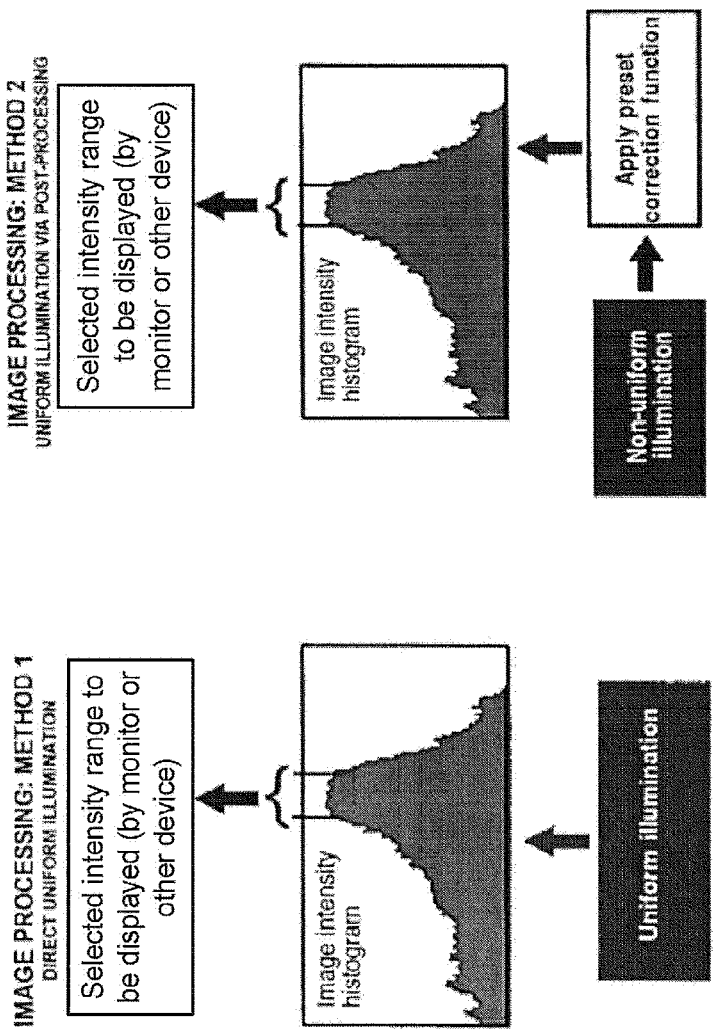

IMAGING SYSTEM AND METHOD FOR ENHANCED VISUALIZATION OF NEAR SURFACE VASCULAR STRUCTURES

BACKGROUND

Technical Field

The present invention relates to imaging systems and methods, and more particularly to a sub-dermal visualization and imaging system and method using Class 1 vertical cavity surface emitting lasers for enhancing imaging of veins and other near-surface vascular structures.

Description of Related Art

There are many applications for imaging objects in or below a turbid medium, such as veins below the surface of the human skin, benign or cancerous tumors below the surface of the human skin, a mass of cancer below the skin, such as IBC (Inflammatory Breast Cancer), or objects below the surface of ice, snow, water or gas.

A common problem associated with the insertion of hypodermic needles and other devices in near-surface veins of a patient is the inability to view or otherwise locate the vein to successfully insert the needle or device therein. The difficulty in visually locating vascular structures with the naked eye is mainly due to the lack of visible photons necessary to penetrate the affected tissue. Vein visualization is currently commonly performed via a naked eye evaluation using mainly two markers. The first is based on the anatomical information as the veins create a protrusion (especially the larger veins) that are located very close to the surface of the skin. The second is based on the higher penetration of the red components of the visible spectrum into the tissue. The red light encountering the veins is strongly absorbed by the blood, and as a result, this location has the appearance of a dark blue-gray color. However, in people with higher melanin content in their skin, the red component is absorbed by the melanin making visualization of the veins even more difficult. In addition, some people have more fat layers between the skin and the veins making the identification of these deeper veins nearly invisible to the naked eye which is often determined by the light both absorbed and scattered at the treatment facility.

Therefore, what is needed is an imaging system and method for enhanced visualization of near surface vascular structures having the following characteristics and benefits over the prior art.

SUMMARY

This summary is provided to introduce a variety of concepts in a simplified form that is further disclosed in the detailed description of the invention. This summary is not intended to identify key or essential inventive concepts of the claimed subject matter, nor is it intended for determining the scope of the claimed subject matter.

In one aspect, the present disclosure relates to a sub-dermal structure visualization system. The system may include a light source adapted to illuminate an imaged area to locate and identify veins and other near-surface vascular structures. An imaging device is arranged to optically capture and relay an image, and an electronic display is configured to receive the image related by the image capturing device. A control unit controls at least one of the spectral and polarization properties of the light source such that the imaged area includes one or more sub-dermal structures within a turbid medium.

In one aspect, the light source is a plurality of Class 1 lasers operated at a drive current between 5 mA and 20 mA. Each of the Class 1 lasers emit light having a spectral range of approximately 700 nm to 950 nm.

In one aspect, the system is configured to be sufficiently portable for use in the clinical and home settings.

In one aspect, the present disclosure relates to a sub-dermal structure visualization system. The system may comprise an illumination module including an illumination module, further including: a plurality of Class 1 vertical cavity surface emitting lasers adapted to substantially uniformly illuminate an imaged area; and a first optical system configured with at least one optical element for controlling at least one of spectral and polarization properties of the near-infrared (NIR) light directed to the illuminated imaged area; an imaging module, further comprising: a second optical system configured with at least one optical element for rejecting at least one unwanted optical components of a detected optical signal returning from the imaged area while passing one or more desired spectral and polarization properties of the detected optical signal; and an imaging device arranged to optically relay an image as provided by a configuration selected from a predetermined magnification and focus configuration and an adjustable magnification and focus configuration; an image acquisition means configured to collect the image from the imaging device and select one or more desired optical components of the detected optical signal, wherein the desired one or more optical components of the detected optical signal comprise a vein visualization signal; an image enhancing means configured to select for a display of the sub-range of intensities of the detected optical signal that comprises the vein visualization signal; and an image display module configured with at least one of an electronic visual display and an image projector that displays the image with at least one display property selected from: an aspect ratio, a desired resolution, and an image contrast that match or exceeds the corresponding values of the image provided by the image enhancing module.

In another aspect and embodiment of the present disclosure a sub-dermal structure visualization system is provided having a camera module within the imaging device comprising at least a battery and a single wire. In a preferred embodiment, the single wire is a USB 3.0 cable. In this aspect, the battery is rechargeable via a wall plug connecting to the imaging device. In a preferred embodiment, the wall plug connects to the imaging device via a USB Type C connection. In this aspect, the imaging device further comprises either a stand or a mount for holding the imaging device in the desired location for hands free operation. The imaging device is also connected to an electronic display device, wherein, in a preferred embodiment, an image is transferred from the imaging device to the electronic display device via a USB 3.0 cable. Also, in a preferred embodiment, the electronic display device is a tablet, which provides for easy and simple operation of the system by users.

In a further aspect, the present disclosure may form a sub-dermal structure visualization method. The method may comprise substantially uniformly illuminating an imaged area including sub-dermal regions thereof with Class 1 vertical cavity surface emitting lasers that are passed through a first optical system including one or more optical elements for controlling at least one of spectral and polarization properties of the light prior to illuminating the imaged area. The method may also involve detecting desired optical components of an optical signal returning from the image area and passed through a second optical system. The second optical system may include one or more optical elements which reject unwanted optical components of the optical signal, wherein the remaining desired one or more optical components of a detected optical signal represent specific portions of the sub-dermal regions where specific anatomical structure of interest is present, wherein the desired optical components of the detected optical signal include a vein visualization signal representing a portion of the optical signal that falls within a sub-range of intensities, relative to intensities of a remainder of the optical signal to assist in visualizing a vascular structure below a skin layer of a patient.

Moreover, in accordance with a preferred embodiment of the present invention, other aspects, advantages, and novel features of the present invention will become apparent from the following detailed description in conjunction with the drawings.

BRIEF DESCRIPTION OF THE DRAWINGS

A more complete understanding of the present invention and the advantages and features thereof will be more readily understood by reference to the following detailed description when considered in conjunction with the accompanying drawings wherein:

FIG. 2 illustrates a method of image processing using direct uniform illumination of an area of interest, according to an embodiment of the present invention;

FIG. 3 illustrates a method of image processing in which uniform illumination is achieved via post-processing of the detected optical signals, according to an embodiment of the present invention;

DETAILED DESCRIPTION

Figure 1:
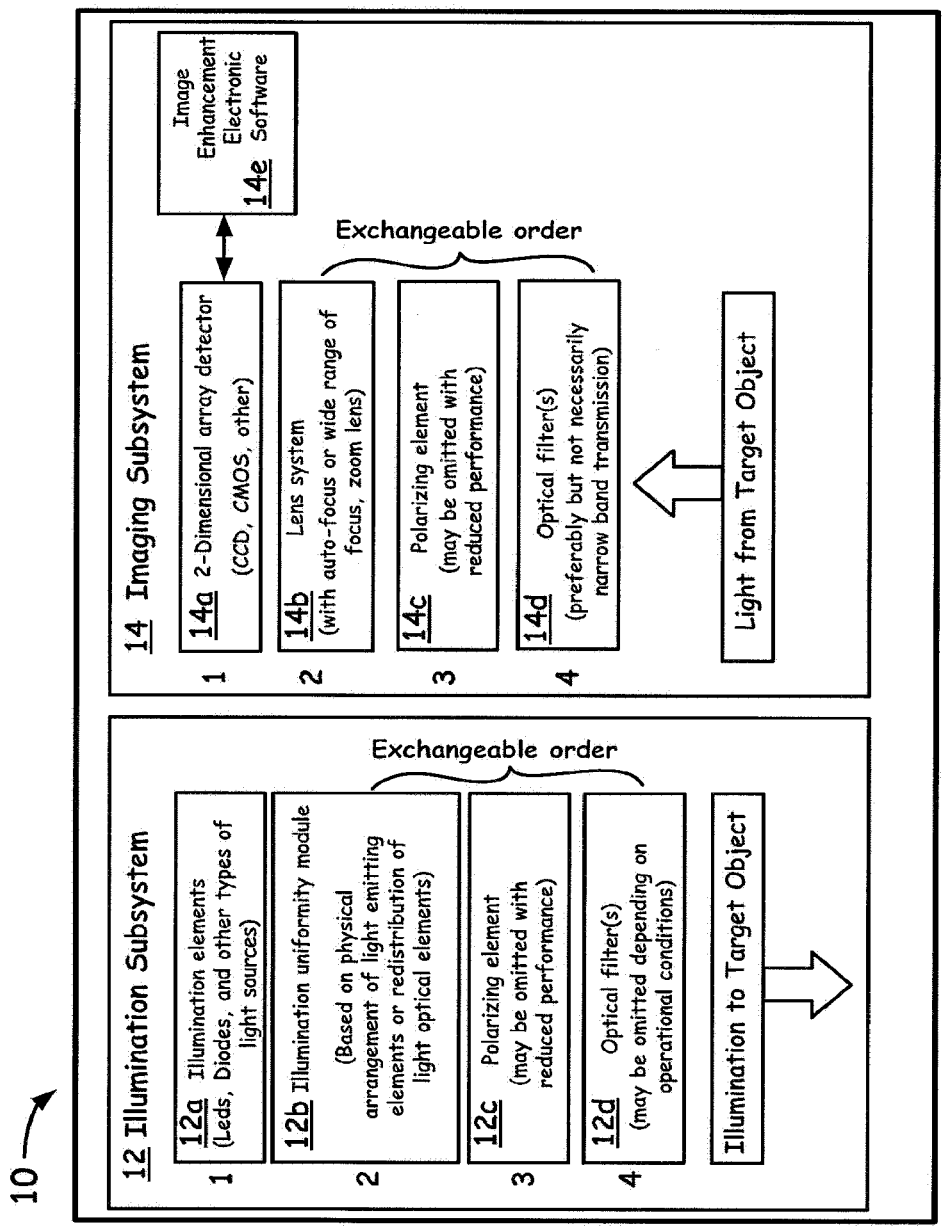
FIG. 1 illustrates a high-level block diagram, according to an embodiment of the present invention.

The specific details of the single embodiment or variety of embodiments described herein are to the described system and methods of use. Any specific details of the embodiments are used for demonstration purposes only and not unnecessary limitations or inferences are to be understood therefrom.

Any reference to "invention" within this document is a reference to an embodiment of a family of inventions, with no single embodiment including features that are necessarily included in all embodiments, unless otherwise stated Furthermore, although there may be references to "advantage's" provided by some embodiments, other embodiments may not include those same advantages or may include different advantages. Any advantages described herein are not to be construed as limiting to any of the claims.

Before describing in detail exemplary embodiments, it is noted that the embodiments reside primarily in combinations of components related to the system. Accordingly, the system components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "approximately."

Accordingly, unless indicated to the contrary, the numerical parameters set forth in the specification and attached claims are approximations that may vary depending upon the desired properties sought to be obtained by the subject matter presented herein. For example, when referring to numerical parameters concerning nanometers (nm), the term "approximately" shall include a range of plus or minus 50 nm. As another example, when referring to numerical parameters concerning milliamperes (mA), the term "approximately" shall include a range of plus or minus 5 mA. At the very least and not as an attempt to limit the application of the doctrine of equivalents to the scope of the claims, each numerical parameter may at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

Near-infrared (NIR) light is known to offer maximum penetration depth in tissues to improve the visibility of the near-surface vascular system. This is a result of reduced absorption of blood and myoglobin. Blood and myoglobin limit the photon penetration depth at shorter wavelengths. Water limits the photon penetration depth at longer wavelengths. The reduced absorption of blood and water enables NIR light to reach and interact with the subsurface veins to bring image information back to be detected by an imaging device. However, although the absorption coefficient of blood in the NIR is reduced, blood remains the main absorbing chromophore, thus causing the veins to appear as darker features independently of the illumination wavelength. In addition, better visualization of the veins using NIR illumination is attained by the reduced absorption by melatonin and the reduced scattering of photons as a function of wavelength.

The problem of visualizing the subsurface vascular system, even with NIR light, arises from a portion of the light injected through the surface which is able to reach the vein before being backscattered to reach the imaging device. Specifically, upon the illumination of the tissue with NIR light a portion of the light will be reflected al the interface between tissue and air due to the change in the index of refraction. The resulting image component (specular reflection image) has no information on the spatial characteristics of the vein since it never interacted with it (i.e., propagated through the vein). The complementary image component contains photons that reached an adequate depth to interact with the vein, thus bearing information about its presence and geometrical characteristics when recorded by the imaging device. This small component of detected light is the Vein Visualization Signal (VVS). The ratio of the VVS to the total detected signal is continuously decreased as the vein is located deeper below the surface of the skin. Visualization of the vascular structure requires a contrast in the recorded image, which is typically presented with the vein having a darker appearance than the surrounding field.

Turning now to the drawings, the various embodiments of the present invention are directed to an imaging system 10, as generally shown by the block diagrams in FIG. 1, and a method in accordance therewith. In particular, FIG. 1 illustrates a system 10 configured with an illumination subsystem 12 which illuminates a target object (as denoted with a large directional arrow) and on return, an imaging subsystem 14 which receives light from the target object (as also denoted with a large directional arrow). Illumination subsystem 12 thus shows example components and/or arrangements of components (denoted as 1, 2, 3, 4), but is not limited only to such disclosed example components and/or arrangements of components. In one example the illumination subsystem 12 may include illumination elements 12a, an illumination uniformity module 12b, one or more polarizing elements 12c, and one or more optical filters 12d, to be discussed in detail below. Imaging subsystem 14 thus also shows example components and arrangements of components but is also not limited to such disclosed components and/or arrangements of components (also denoted as 1, 2, 3, 4). The imaging subsystem 14 in one example may include one or more array detectors 14a, a lens system 14b, one or more polarizing elements 14c, and one or more optical filters 14d, also to be discussed in detail below. Imaging subsystem 14 within system 10 also shows image enhancement electronic hardware and software 14e (i.e., a processing means), as generally illustrated via an operational block.

Further illustrated in FIG. 1 is the method of embodiments herein will respect to system 10, the method involves using polarization filtering and illumination with NIR light for enhanced visualization (i.e., improved image contrast) of veins and other vascular and sub-dermal structures located below the skin. In particular, NIR light is used for illuminating an area of interest (AOI) because it is capable of maximum photon penetration depth in tissues. In addition, the specular reflection image component is removed using polarized NIR. Illumination 111 particular, since the specular reflection image component arises from photons that have undergone a single reflection event per detected photon, these photons maintain their polarization state. Therefore, by using polarized illumination and detecting the orthogonal image components, the specular reflection image component can be nearly eliminated. In this regard, the present invention may incorporate methods for reducing or eliminating part of the signal using polarization methods and image processing via acquisition of images at different wavelengths, described in the following references: S. G. Demos and R. R. Alfano, "Optical Polarization Imaging" Applied Optics, 36, 150-155, 1997; R. R. Alfano and S. G. Demos, "Imaging of Objects Based Upon the Polarization or Depolarization of Light", U.S. Pat. No. 5,929,443; and R. R. Alfano and S. G. Demos, "Imaging of Objects Based Upon the Polarization or Depolarization of Light," U.S. Pat. No. 5,847,394, all of which are incorporated by reference herein.

In further detailing system 10 in FIG. 1 the imaging system 10 first includes an illumination system, component module, or sub-system 12 capable of illuminating an AOI with NIR light provided by illumination elements 12a. The illumination elements 12a may include, but are not limited to, a NIR light source, such as one or more or a NIR lasers that operate in the NIR spectral range. As additional illumination light source embodiments, a conventional infrared emission source that is heated to emit a continuous band of optical radiation, e.g., an infrared igniter source element, incandescent sources filtered for NIR, and supercontinuum lasers (which emit light in the entire 400-2400 nm wavelength range), etc. can also be incorporated into the embodiments herein if desired.

Preferably, however, illumination elements 12, a laser diode (often low power light sources), is desired based on their compact nature. The laser diode may be designed or otherwise configured (properly modified) to provide nearly uniform illumination of the AOI during operational conditions, such as by being appropriately positioned with respect to the image acquisition component, and/or being accompanied by additional optical elements such as light diffusers that enable near uniform illumination of the AOL Furthermore, as part of the illumination subsystem 12, an optical system is provided including one or more optical elements which control at least one of spectral and polarization properties of the NIR light, and which are positioned so that NIR light output from the light source is passed through the optical system prior to illuminating the imaged area. The optical system may include such optical elements as an illumination uniformity module 12b, polarizers 12c (broadband and/or near-field polarizers), optical filter 12d (including one or more of narrowband interference filters, bandpass filters and long wave pass filters, waveplates, etc.) to control the illumination light spectral and polarization properties.

The following is additional description regarding sub-ranges specific to different classes of people (dark/light skin, fat content baby, low blood pressure, etc.) The illumination source uses light mostly in the NIR spectral range from approximately 650 nm to approximately 1400 nm. The illumination bandwidth can be narrow (on the order of 1 nm or less) or broader (on the order of 20 nm or more) and can be determined by specific requirements of the design such as the particular intended use and/or cost of system components. In particular, for imaging individuals with darker skin, the optical performance may be associated with illumination around 850 nm and this illumination can be relatively broad. To image individuals in which a fat layer is located between the skin and the veins (such as more obese individuals), illumination in the 700 nm or 790 nm spectral range, and within a relatively narrow band (e.g., on the order of 10 nm or less) is required to use the narrow spectral band where absorption by fat is minimal. Other case examples may require different illumination wavelengths for optimal vein visualization and imaging.

Figure 6:
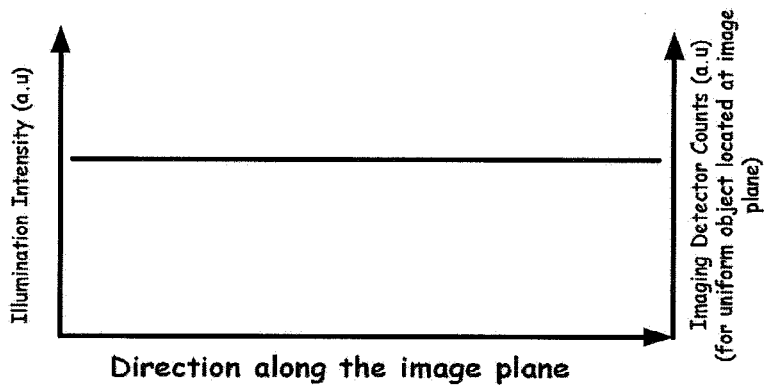
FIG. 6 illustrates a plot of illumination intensity and imaging detector counts versus a direction along the image plane to illustrate nearly uniform illumination of an imaged area, according to an embodiment of the present invention.

Within the imaged area, there can be (and typically is) a large range of intensity recorded by the imaging device. However, in a particular location within the imaged area, the VVS (vein visualization signal) is within a small range of intensities compared to the signal obtained those portions of the imaged area that do not contain veins. To achieve a simple image enhancement method, the present invention displays only a narrow range of intensities containing the VVS, as shown in FIGS. 2 and 3. This is a cost-effective method that does not require digital image processing. However, the VVS signal intensity may be similar throughout the imaged area. This requires a nearly uniform illumination of the imaged area, as defined in FIG. 6. Even with digital image processing, the uniform illumination beneficially offers better results. It is to be appreciated that as seen in FIG. 2, uniform illumination is provided directly, whereas in FIG. 3 uniform illumination is produced by post-processing, i.e., applying a correction function to correct for the non-uniformity.

The illumination uniformity module 12b may be based on (a) physical arrangement of light emitting elements or (b) redistribution of light via optical elements. In case (a), the uniformity illumination module 12h is most often positioned in position 2 of FIG. 1 In case (h), it depends on if the optical element causes depolarization of light or not If it does not cause depolarization of light, then the illumination uniformity module 12b, the polarizing element 12c and the optical filter 12d can be placed in positions 2, 3 and 4 as shown in FIG. 1 If the optical element causes depolarization of light, the polarizing element 12c must be positioned after the uniformity illumination module 12b while the optical filter 12d can be positioned before module 12b or element 12c, in between the module 12b and element 12c, or after the module 12b and element 12c. It is to be noted that in the above discussion, it is assumed that the optical filter 12d does not cause depolarization of the illumination light If it does, then the polarizer 12c is often positioned after the optical filter 12d (however such fitter may not be selected for a system that is based on the present invention). For the various permutations of ordering the optical components of the illumination sub-system 12, the following describes some of the criteria/requirements which make the various ordering schemes (for modules 2A, not 1) possible. The illumination element 12 (i.e., source) is always placed in position 1. The polarization elements 12c and the optical filter 12d can be exchanged in position. Typically, the optical filter 12d is in position 4, so this subassembly is also acting as a barrier with the environment (as the fitter can be selected from a glass or other high strength material).

Imaging Device. Component, Module, or Sub-System

Although briefly described above, the imaging device, component, module, or sub-system 14 of the present system 10, in further detail also includes an image acquisition device, component, module, or sub-system 14a. As illustrated in an example, this may be a digital camera system or 2-dimensional array detector, or an array camera that can be incorporated herein, e.g., as generally shown in FIG. 1 that detects a portion of the illumination light that is reflected from the AOI towards the imaging subsystem 14. The imaging subsystem 14 also incorporates a lens system 14b for imaging the AOI onto a detector array such as a CCD or CMOS device, of the image acquisition device 14a. The imaging lens may be designed to provide an in-focus image over a wide range of distances from the system 10 so that the AOI can be correspondingly located within this range. This allows the operator to acquire images while the relative position of the device w the AOI can be changed in both the separation length and the angle with respect to the AOI surface. Furthermore, the lens 14b can provide adjustable zoom (magnification) and focus that can be selected by the operator. Thus, such operations allow a user, as example embodiments, to select in a predetermined manner the desired magnification and focus or in an automatic selectable configuration, provide for the desired magnification and focus for the image acquisition device.

Furthermore, optical modules, including one or more optical elements that often entail polarization control elements 14c and optical filters 14d, are configured to allow rejection of unwanted one or more optical components from the detected signal, and may be positioned before or after the lens system 14b in order to increase the relative intensity of the VVS compared to the total detected signal by the imaging detector 14a. Such unwanted one or more detected signal components arising from the illumination of the AOI by the systems illumination source can cause degradation of the image contrast between the veins and the surrounding tissue. In addition, these system optical elements are selected to reject or reduce one or more optical components from ambient tight such as from fluorescent or white light emitting diode (LED) light sources or from Incandescent or halogen light bulb, or even from indirect light from the sun.

In this manner, the image acquisition and processing components of the imaging subsystem 14 function to detect the portion of the illumination light that is reflected towards the imaging subsystem 14 of FIG. 1, after it is passed through additional optical elements. For example, the passed through optical elements can include: optical filters 14d and polarization control elements 14c: that allows rejection of unwanted optical components, such as, light components that can cause degradation of the contrast between the veins and the surrounding tissue and reject components from ambient tight. Commercially available security cameras with night vision capabilities may, as example components, be selectively used for the illumination and image acquisition components based on predetermined criteria for the lens design, the LED emission wavelength, the ability for wireless video transmission, portability, etc.

It is to be appreciated that with the imaging subsystem 14, while the lens system 14b, the filter 14d and the polarizer 14c are generally exchangeable in position, some lenses may cause depolarization (or rotation of the polarization) of the propagating light. In this case, the polarizer 14c is often positioned before the lens system 14b. It is to be understood, however, that the filter 14d can still be positioned anywhere (positions 2-4) within the imaging subsystem 14 assuming that it does not change the polarization state of the light.

The imaging subsystem 14 of the system 10 of the present invention may also include an image processing device, component, module, or sub-system that is designed to provide contrast enhancement of the veins via either electronic components or via digital image processing means to further enhance the visualization of the veins. This may be implemented using additional signal electronics and/or software 14e. The additional electronics and/or software may be provided for post-processing the detected signal to further enhance image contrast. This may involve various means including the mathematical processing of the image or the selection for display of only a range of intensities within the dynamic range of the imaging device. Such image processing can be provided via electronic or hardware (e.g., a toggle switch) components located on the imaging and/or display system or can be attained via computer software, as to be discussed in further detail below.

Figure 4A:
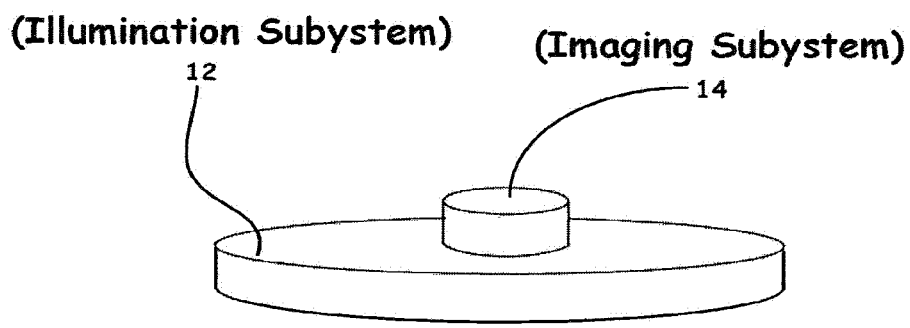
FIG. 4A illustrates the relative positions of the imaging subsystem and the illumination subsystem, according to an embodiment of the present invention.
Figure 4B:
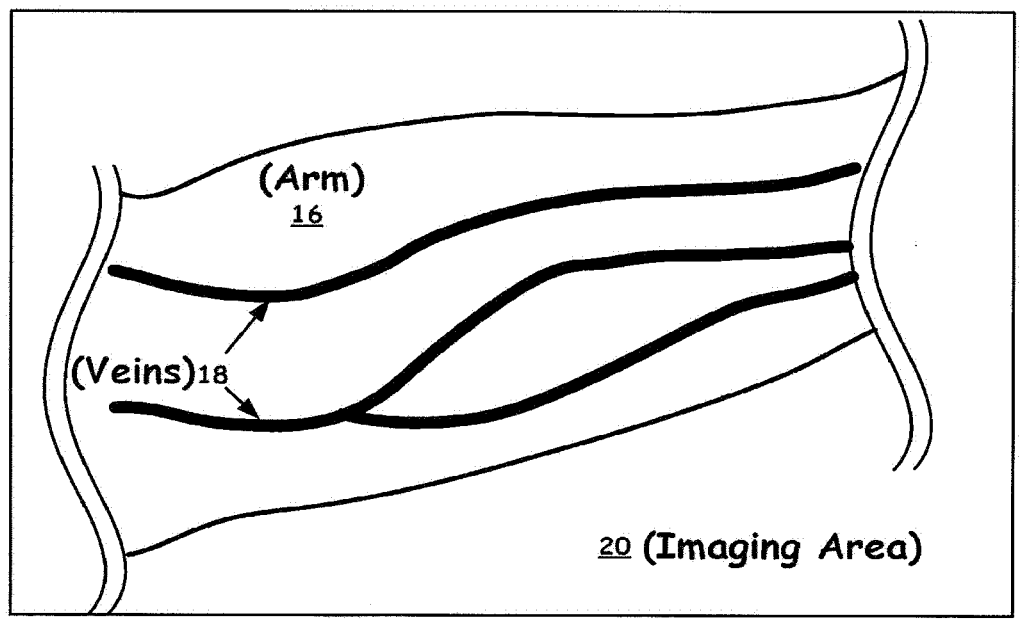
FIG. 4B illustrates an imaged area of interest (AOI), according to an embodiment of the present invention.
Figure 5A:
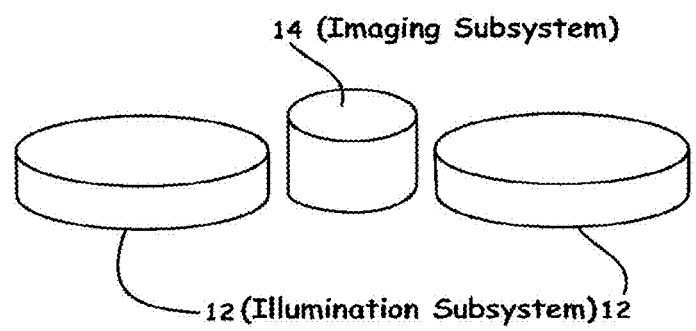
FIG. 5A illustrates an embodiment where two illumination subsystems are used to illuminate an imaging area, according to an embodiment of the present invention.
Figure 5B:
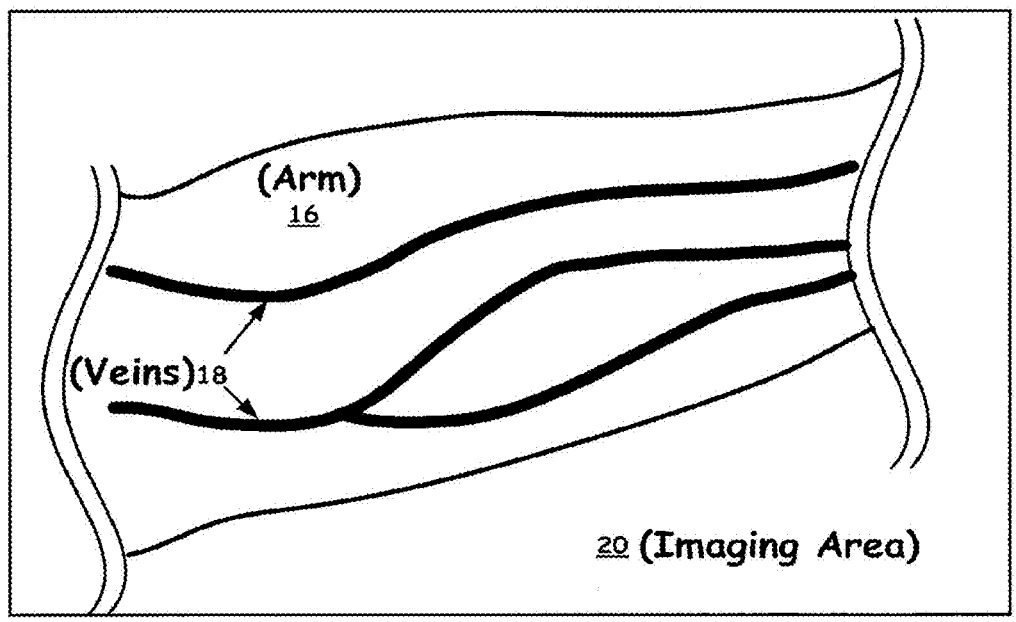
FIG. 5B illustrates an imaged area of interest (AOI), according to an embodiment of the present invention.

Various aspects of the signal collection light for image formation may be controlled including the spectral content of the light and the polarization of the signal light. The polarization of the signal light must be the orthogonal polarization state from the illumination polarization state (which can be linear, circular, elliptical etc.). Furthermore, FIG. 4A shows an example configuration wherein the imaging subsystem 14 and the illumination subsystem 12 may be coupled in close proximity (e.g., coupled together, even co-linearly). FIG. 5A shows an additional example configuration wherein the imaging subsystem 14 and the illumination subsystem 12 can be de-coupled. It is also to be appreciated that FIG. 5A also shows, for example, a non-limiting embodiment wherein two illumination subsystems 12 are being used to illuminate an imaging area. It is also to be noted that white the components (e.g., illumination subsystem 12 and imaging subsystem 14) are depicted with circular geometries in the examples, the components can also be configured in other geometric component styles, such as, rectangular, square, elliptical, etc., where warranted to provide the working embodiments. It should be further noted that FIG. 4B and FIG. 5B illustrate imaged areas (i.e., imaging area 20) of an arm 16 and its vein structure 18, via the example embodiments generally shown in FIG. 5A and FIG. 5A.

As previously discussed, within a given area of interest being imaged, there can be (and typically is) a large range of intensity recorded by the imaging device 14a However, in a particular location within the imaged area, the VVS will fall within a small range of intensity compared to the signal from the imaged area that does not contain veins. To achieve a simple image enhancement method, the system 10 of the present invention displays only a narrow range of intensities containing the VVS, as shown in FIG. 2 and FIG. 3 This is a simple and inexpensive method that does not require digital image processing. The imaging subsystem 14 may additionally include a monitor or other display system for graphically displaying the image within the small range of intensities. While the image has no color information (monochrome) it may be displayed in grayscale or in color. It is to be appreciated that the display may be attached to other components of the imaging subsystem 14 or it may be separated as a standalone component of the imaging system.

Use of Fiducial Marks/Elements to Enhance Spatial Correlation

Figure 7:
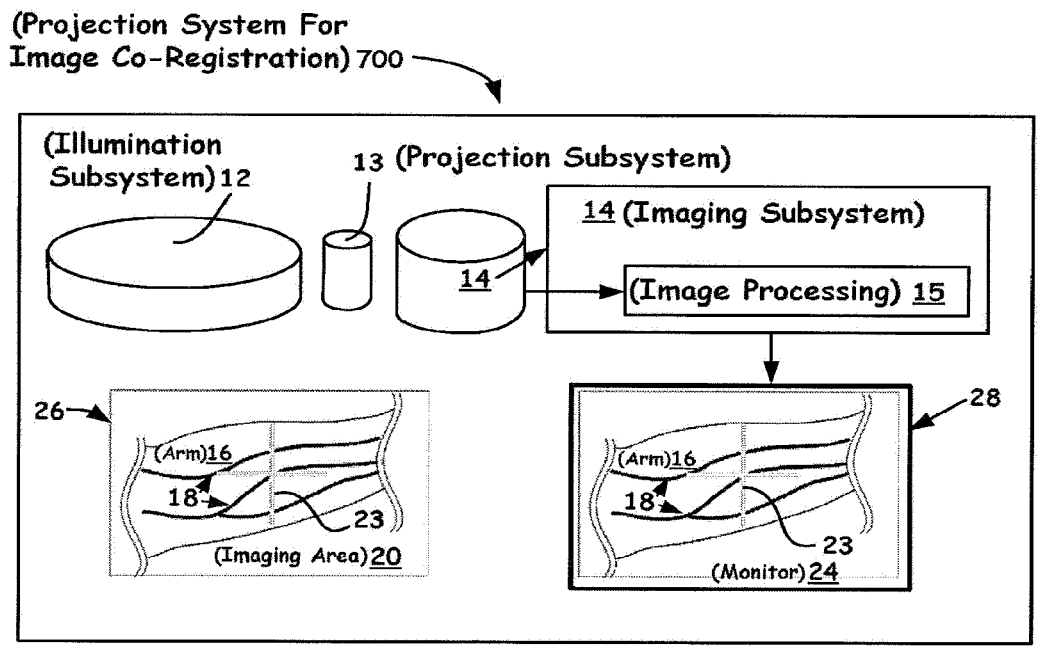
FIG. 7 illustrates an example projection system for co-registration, according to an embodiment of the present invention.
Figure 8A:
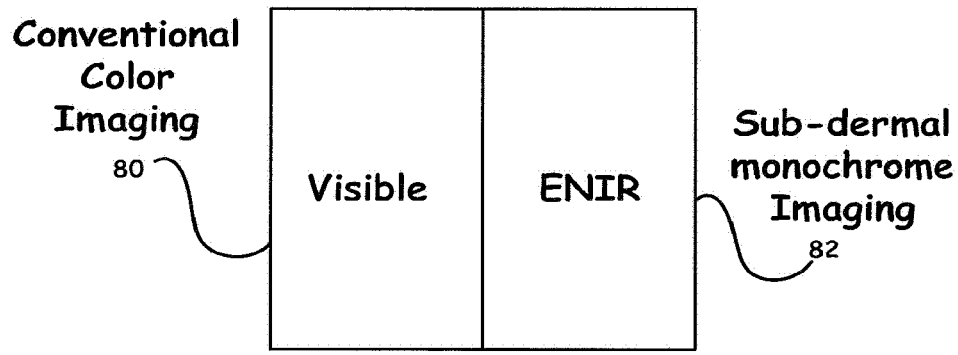
FIG. 8A illustrates a general depiction of a system that requires that the visible images and enhanced near-infrared images are captured simultaneously.
Figure 8B:
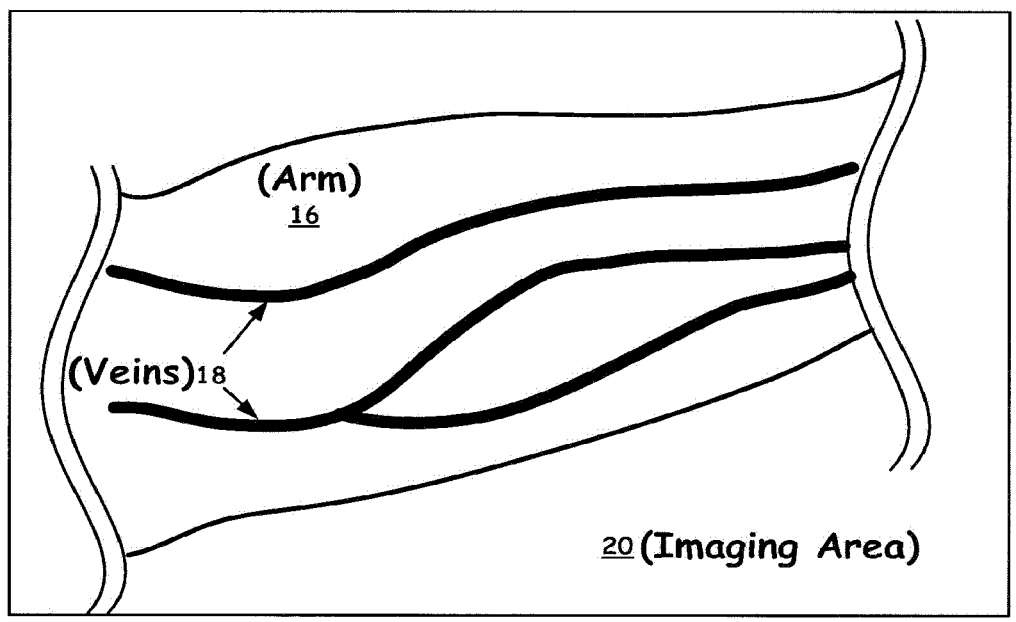
FIG. 8B illustrates an imaged area of interest (AOI), according to an embodiment of the present invention.

FIG. 7 shows an example co-registration illumination system 700 to include subsystem 12, imaging subsystem 14, and image processing 15 means of captured imaged areas 20 (i e., of an arm's 16 desired vein structure 18). The operator can visualize the vein 18 structure via some monitor 24 screen, as known to those skilled in the art, either attached or detached from the imaging subsystem 14. The co-registration itself is enabled via a projection subsystem 13 for marker location of an area. In particular, to enhance the ability of the operator to correlate the image to the visual perception, specific markers (i e., crosshairs 23, as shown in FIG. 7) on the arm 16, veins 18, can be used that are projected on the imaged area 20, as shown in the left lower depiction 26 of FIG. 7 and displayed on the monitor 24 (or correlated to a specific location within the image presented in the monitor, such as the center of the image), as shown in the right lower depiction 28 of FIG. 7. This can include but is not limited to, low power laser sources such as one or more red laser pointer(s) that help establish this correlation. Specific examples of methods that may be used to display the cross-hairs in the example embodiments herein may involve, without limitation, a mask on CCD, or using a laser pointer which is detected by the imaging subsystem 14.

To demonstrate further detail, fiducial marks, such a cross-hairs 23 or bright spots, can be used to allow the user to associate the visual perception with the images obtained by the system 10. This is necessitated by the fact that the vein structure observed in the image obtained by the system 10 may be difficult to associate with the naked eye view of the target area (such as an arm) Using fiducial marks which are projected onto the target area, that is also highlighted in the image obtained by the system 10, beneficially assists the operator to locate the area in the arm that correlates to a specific location of interest in the image.

The image display fiducials may be generated during the imaging processing step 15, as shown in projection system 700 of FIG. 7, which is after the image was recorded and transmitted. This can be achieved either by digitally processing the image to enter the fiducial markings or even by producing a marking on the display, such as the center point of the image, using simpler physical methods.

The fiducial may be embedded during the image acquisition process incorporating a variety of methods. One of the methods include using the projected light on the target area to form the fiducials, which contain spectral components that can be recorded by the imaging device. This enables direct visualization of the position of the fiducials during image display. Another method involves inducing the fiducials on the array detector 14a, as generally depicted in FIG. 1, 'which is capturing the image. This can be achieved by deactivating a number of pixels to form dark points (generating dark spots or dark lines) or by using a mask in front of the detector 14a that reduces or obstructs the collected signal to form the fiducials on the display.

The visualization embodiments described above offers enhanced visualization of structures located below the dermis, such as veins located 1 mm up to 1 cm (or more) below the skin in humans. As the visual perception of the human eye is based on the interaction of light with tissue in the visible spectral range, the features observed in the sub-dermal structure visualization embodiments described above are largely not visible to the naked eye. It is also possible that certain features that are visible to the naked eye are not visible by the sub-dermal structure visualization system. It may, therefore, be beneficial to devise methods that can provide both types of images to the operator. Specifically, a beneficial integrated system may contain the capability of substantially simultaneously acquiring (recording) conventional color images in combination (if desired) with the sub-dermal structure visualization images. The following discussion provides insight as to the enablement of such methods in technically realistic and cost-effective designs.

FIG. 5A illustrates the approach which requires that both, the visible image 80 and the enhanced near infrared (ENIR) image 82 (acquired using the methods described above) are acquired "substantially simultaneously." HG. 8B again shows the capability of an image of the arm 15 and veins 18 within an imaging area 20. It is to be appreciated that the term "substantially simultaneously" as defined herein, refers to the acquisition of images of each type in a rate that is fast enough to be perceived by a human operator as continuous (on the order of 10 frames per second) or quasi-continuous (on the order of 1 frame per second). These images can he provided to the user/operator via the following possible basic methods and/or combinations of these basic methods:
  a) There are two separate sensors that work independently to acquire each image type;
  b) The same sensor acquires sequentially each type of image;
  c) The same sensor acquires simultaneously both image types.

It should be noted that the term "sensor" refers to an integrated imaging device which can be comprised of: a) a single two dimensional detector (such as a monochrome CCD sensor), b) a coherent array of monochrome detectors recording images at different spectral ranges (such as three-CCD camera which uses three separate CCDs, each one taking a separate measurement of the primary colors, red, green, and blue), c) a single two dimensional detector containing different types of pixels designed to record different parts of the optical spectrum (such as in color sensors where different groups of pixels record the three primary colors, red, green and blue) or d) a specialty sensor designed to acquire multi-spectral images.

Furthermore, upon acquisition of each image type, each image type can be, using hardware and software apparatus, for example, displayed separately in different monitors or other type of display device or the two image types can be fused together in a single image that displays in an effective manner the information contained in both images. For the more accurate co-registration of both images during the image fusion processor for seamless, simultaneous display, the use of a single optical imaging element (imaging lens) to relay the image of the object to the imaging sensor(s) may be the most effective method (although not the only method). It is also to be appreciated that a particular sensor is often configured (i.e., associated/coupled) with the desired filter designed for spectral selection and purification (e.g., select and/or eliminate undesired optical components). Moreover, the desired filter(s) can be alternately configured for visible light or ENIR optical components and also alternately positioned in front of the desired filter. In addition, the same sensor (i.e., the particular sensor) can also be configured optically to collect simultaneously the visible or the ENIR image components w provide an image that contains both image components.

Figure 9A:
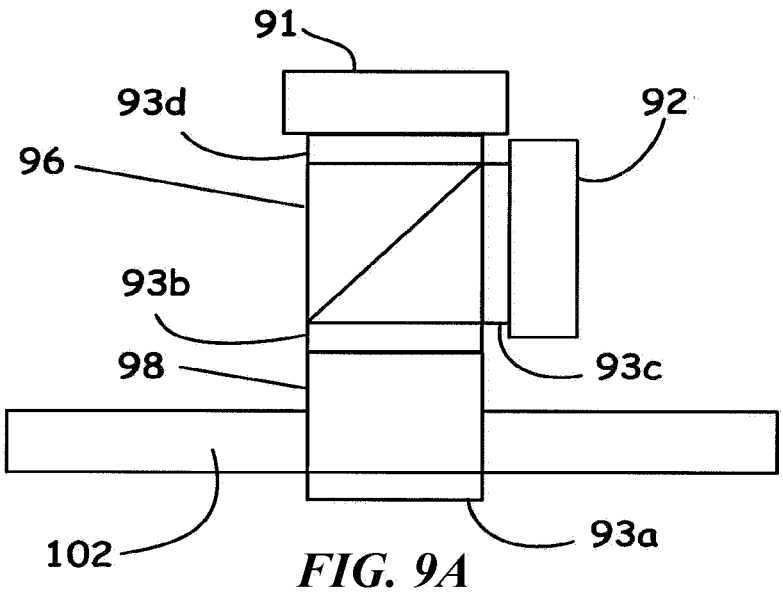
FIG. 9A illustrates an exemplary illumination subsystem generally indicating where various optical elements may be positioned in a two-imaging sensor configuration.
Figure 9B:
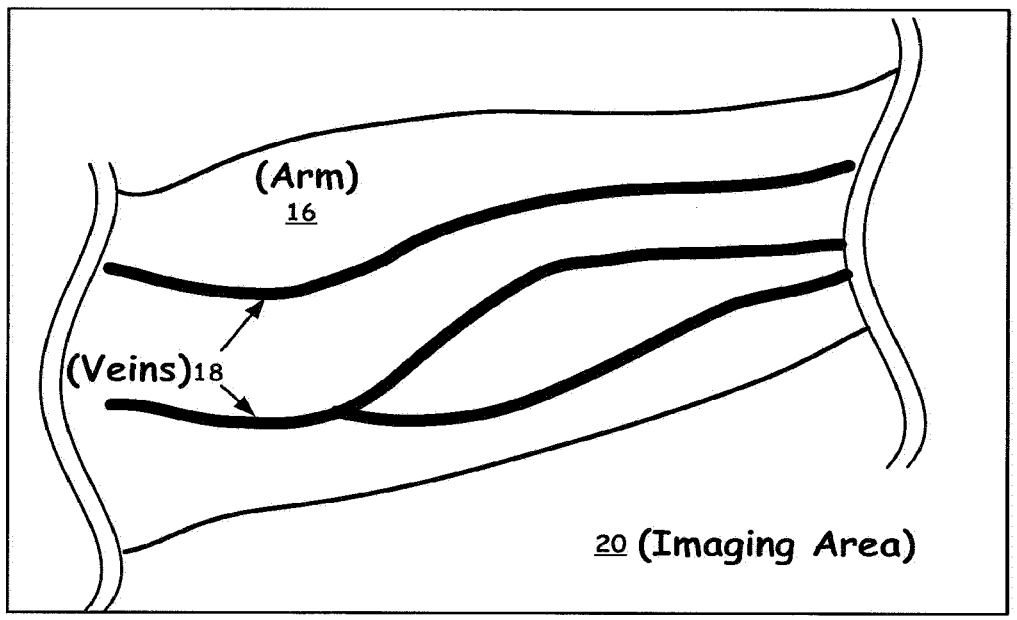
FIG. 9B illustrates an imaged area of interest (AOI), according to an embodiment of the present invention.

The following discussion provides, for example, technical solutions in the context of the sub-dermal structure visualization methods described for the present embodiments. In particular, FIG. 9A shows an exemplary illumination subsystem which, as described before, contains illumination elements (such as LEDs), an illumination uniformity Module (which can be integrated into the illumination elements), a polarizing element and optical filters. FIG. 9B again shows the capability of an image of the arm 15 and veins 18 within an imaging area 20. In detail, FIG. 9A shows at least two imaging sensors 91, 92, optical elements (e.g., modules) 93a, 93b, 93c, and 93d, a beam splitter 96, a lens system 98 and the illumination subsystem 102. The illumination elements may include specific elements that provide illumination in the visible spectrum to complement the elements providing illumination in the NIR spectral region used for sub-dermal imaging and aid ambient visible light. The optical filter may not be used, but the polarizing elements may be used as they can enhance the quality of both types of recorded images. The visible light illumination elements are not required (hut they can be used to enhance the visible image) as the ambient visible light can be used for the illumination of the target area.

FIG. 9A also shows example locations where various optical elements (OLs) may be positioned. These can include, for example, a polarizer (with its polarization orthogonal to the polarization state of the illumination) and optical filters that select and/or further purify the spectral content of the collection by the lens system light to be used for image formation by each sensor. For example, such filters may allow the visible light to reach the sensor used to record the visible image but eliminate the NIR light.

The system shown in FIG. 9A can also be used in a mode that allows subtraction of the background light reaching the sensors. This background light includes all light that does not originate from the illumination elements of the illumination subsystem (such as the ambient light). One simple non-limiting method (but not the only one) to execute such a task is to consecutively acquire two images by one (e.g., sensor 91) or both sensors (e.g., sensor 91 and sensor 92) when the illumination elements are turned on and when the illumination elements are turned off. The second image contains image arising from ambient light while the first image contains image arising from both, the ambient light and the light originating from the illumination elements. Subtraction (or other suitable processing) of the two images can effectively remove the image component arising from the ambient light (which will be equal in intensity in both recorded images) and provide an image arising only from the exposure of the target area to the tight of the illumination elements.

Figure 10A:
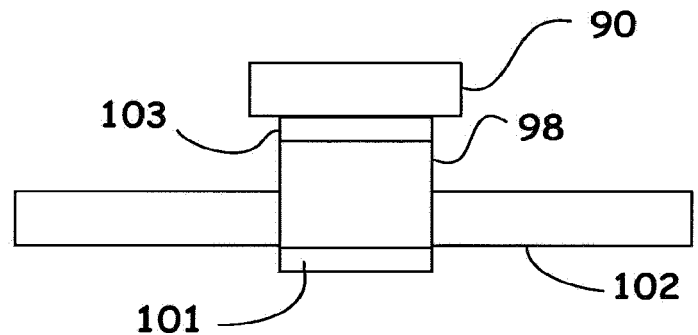
FIG. 10A illustrates an illumination subsystem in a one imaging sensor configuration.
Figure 10B:
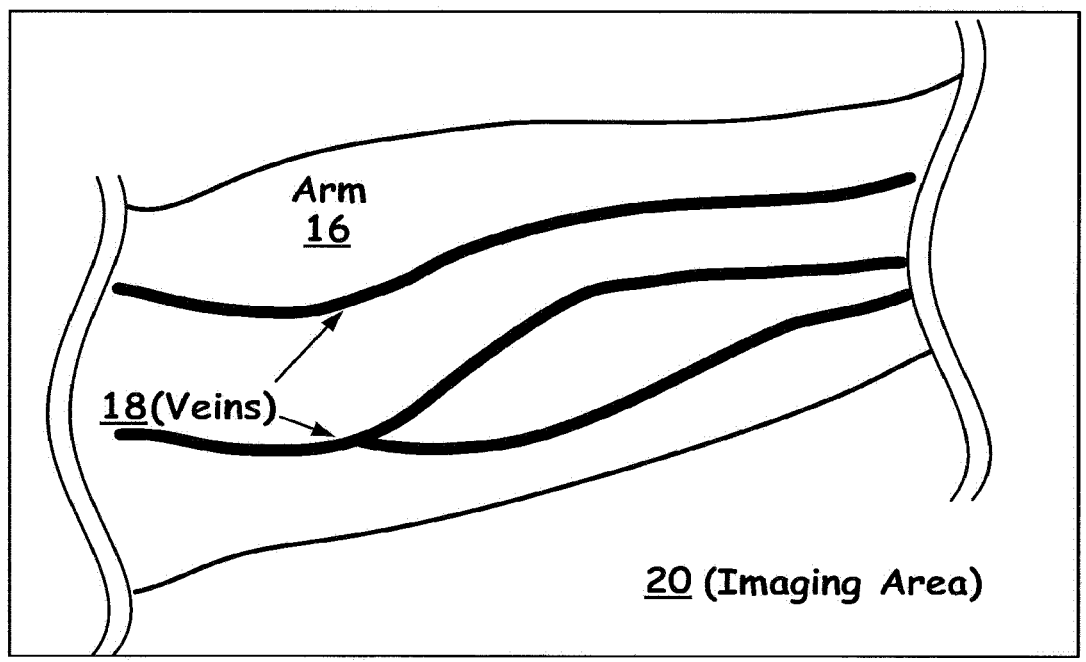
FIG. 10B illustrates an imaged area of interest (AOI), according to an embodiment of the present invention.

FIG. 10A provides a schematic layout of the system that utilizes, in this example mode, one imaging sensor 90, optical elements (e.g., modules) for the acquisition of the conventional visible (color) images and the acquisition of the ENIR sub-dermal images. FIG. 10B once again shows the capability of an image of the arm 15 and veins 18 within an imaging area 20. Such a sensor 90, as shown in FIG. 1 OA is designed to separate and record in different sets of pixels the different spectral components of the visible light such as the red, blue and green (RGB) components used for color image recording (video recording or in color photography) in the electronics industry. In addition, this sensor may be able to record the near-infrared image of the subdermal structures. His well known that currently available color sensor (such as CCD and CMOS color image sensors) are also sensitive and capable of recording light in the NIR spectral region and most commonly in the 800-900 nm spectral region. For this reason, these sensors are equipped with a NIR blocking filter when used in conventional color video or photography applications to allow only the visible light to reach the detector. However, by removing this filter, a conventional color image sensor can also detect the NIR light.

Similar to the embodiment shown in FIG. 9A, an exchangeable filter set may be used in the embodiment of FIG. 10A to allow the sensor to record either:
 a) the visible color image by placing a filter in front of the sensor that eliminates the NIR light and transmits the visible light; or
 b) the ENIR image by placing a filter in front of the sensor that eliminates the visible light and transmits the NIR light.

In contrast to the design depicted in FIG. 9A, the two images are not recorded independently in the design depicted in FIG. 10A as in each instance, either the color or the NIR image are recorded or the sum of the color and NIR image components. As a result, the image can be displayed as follows:
 a) The operator can select which image to be displayed;
 b) Each image is alternately (up to the desired video rate) displayed on the same monitor;
 c) Alternately display the two images in two different monitors (with additional hardware and/or software to separate the two images);
 d) The image acquisition and display can be very fast, up to the desired video rate, so the alternate acquisition may not be perceived by the operator to whom it will appear as viewing two separate images at video raw;
 e) Can be fused into a single pseudo-color image containing both image components.

In the embodiment of FIG. 10A, a proper filter may be used (such as a filter that allows the visible and part of the NIR spectrum to pass and reach the sensor) to allow the sensor to simultaneously record and form images using both, the visible and ENIR components. As mentioned earlier, the currently available color sensor is also sensitive and capable of recording light in the NIR spectral region and most commonly in the 800-900 nm spectral region. By removing the NIR light blocking filter, a conventional color image sensor can also detect the visible and NIR light in the approximately 800-900 nm spectral range. In addition, the pixel used to record the red color are also able to record the NIR light up to approximately 900 nm. Therefore, one can devise various methods to simultaneously record the visible and ENIR components in a conventional color imaging sensor. This approach also fuses the visible and the ENIR image components. The resulting image appears to be "color" but also contains the ENIR component. Such method in various specific implementations can be used to provide enhanced visualization of the veins while the color image components are also visible and presented to the user.

FIG. 10A also shows the incorporation of various optical elements (OLs). These include a polarizer 101 (with its polarization orthogonal to the polarization state of the illumination) and optical filters 103 that select and/or further purify the spectral content of the collected light by the lens imaging system The order of the location of one or more optical elements (OLs) ml, 103, lens system 98, and exchangeable filter set (not specifically detailed) is not fixed, and any of these elements can be positioned in front of the other as needed by the specific design.

The system shown in FIG. 10A can also be used in a mode that allows subtraction of the background light reaching the sensors using methods similar to those described for the design depicted in FIG. 9A. This background light includes all light that does not originate from the illumination elements of the illumination subsystem. One simple method (but not the only one) to execute such a task is to consecutively acquire two images while the illumination elements are turned on and when the illumination elements are turned off the second image arises fh-1m ambient light while the first image contains image arising from both, the ambient light and the light originating from the illumination elements. Subtraction (or other suitable processing) of the two images can effectively remove the image component arising from the ambient light and provide an image arising only from the illumination elements that will be of higher quality. This method of background subtraction can be used when the sensor operates in the visible image mode, the ENIR imaging mode or in the fused image mode as described above.

Image Display

The image display unit can be attached or detached from the illumination subsystem and/or imaging subsystem. The image acquisition, processing, and display may be fast enough to be perceived by a human operator as continuous (on the order of 10 frames per second or higher) or quasi-continuous (on the order of 1 frame per second). The display module may have the following characteristics:
 a) The image display area is within a range that the operator can comfortably view the vein structures in the arm. Although this may vary with the operator and working environment a specific example may be a monitor having a diagonal dimension between approximately 7 and 10 inches when the viewing operator is located up to 100 cm to 150 cm from the monitor. In a preferred embodiment, the distance from the operator to the monitor is approximately 40 cm.
 b) The image display has pixel resolution that matches or exceeds the pixel resolution of the image as provided by the sensor.
 c) The image display has an aspect ratio that matches the aspect ratio of the image provided by the sensor.
 d) The image display has a sufficiently high Luminance and Contrast Ratio that can support or enhance the image contrast provided by the image enhancement module.

Communications and Data Storage Device, Components, Etc.

The imaging subsystem 14, as shown in FIG. 1 of the present invention, may additionally include a communication component for transmitting the image to the display. This can he achieved, for example, with wired or wireless communication means, as discussed in detail below. The image can be stored in computer memory or other types of storage media (discussed below) in the form of still images or a sequence of images (such as movies) The transmission and recording system can include the recording of images and ambient sound, or it can incorporate two-way sound between the display and the imaging devices. The latter is applicable 'when the display (or an additional display reproducing the image of the first display) is in a remote location (as further detailed below) so that instructions from the observer of the second display can be transmitted to the operator of the imaging device.

In a preferred embodiment, the image enhancement software 14e is the software code for image applications, such as changing the contrast and brightness of an image. Furthermore, in at least one embodiment, the software utilizes a contrast enhancement algorithm.

Even more particularly, the operation of the image enhancement software 14e in addition to the operation of the system 10 and components therein system 10, as generally shown in FIG. 1, can be controlled and respective data can be acquired by a control and data system of various circuitry of a known type, which may be implemented individually or a combination of general or special-purpose processors (digital signal processor (DSP)), firmware, software to provide instrument control and data analysis for the system 10. This also includes the aforementioned image enhancement software 14e, and/or related instruments, and hardware circuitry configured to execute a set of instructions that embody the prescribed system 10, data analysis and control routines of the present invention.

It is also to be appreciated that instructions to activate or deactivate the embodiments herein, and/or the exporting/displaying/outputting the instruments characteristics, etc., may be executed via a data processing based system (e.g., a controller, a computer, a personal computer, a handheld device, etc.), which includes hardware and software logic for performing the instructions and control functions.

In addition, such control functions can also be implemented as provided by a machine-readable medium (e.g., a computer readable medium). A computer-readable medium, in accordance with aspects of the present invention, refers to non-transitory media known and understood by those of ordinary skill in the art which have encoded information provided in a form that can be read (i.e., scanned/sensed) by a machine/computer and interpreted by the machine's/computer's hardware and/or software.

System 10 shown in FIG. 1 also can be configured with a communication interface to include a wireless (as briefly discussed above) transmitter/receiver unit that is configured to transmit signals from a processor to other devices and to receive signals from other devices. For example, the communication interface permits a processor to communicate with other devices via a wireless network that includes multiple devices connected to the network, and/or via a direct connection to another device. Such a configuration can enable the system 10 to communicate with a central computer system to update the database of reference information stored in a storage unit. In addition, the processor can also, if desired, contact the central computer system to receive updated reference information about, as one example, a particular patient, and such a configured processor can also receive automatic updates that are delivered by the central computer system.

In some embodiments, system 10 can be connected to other devices over other types of networks, including isolated local area networks and/or cellular telephone networks. The connection can also be a wireless connection or a physical coupling.

As non-limiting examples of a wireless connection, such an arrangement can include commercial wireless interfaces, such as but not limited to, radio waves (Wi-Fi), infrared (IrDA), or microwave technologies that also allow integration into available portable personal devices, such as, but not limited to, cell phones, pagers, personal identification cards, laptops, etc.

The wireless network can, for example, be configured with Bluetooth, which operates in a globally available frequency band (i.e., 2.4 GHz), ensuring communication compatibility worldwide, or Electronic and Electrical Engineers IEEE technologies (e.g., IEEE) 802.11a or IEEE 802.11b) as the communication means based on its present common use in both business and home environments. Moreover, other protocols for wireless, such as IEEE 802.15, IEEE 802.16, GPS, 3G and others, may also be configured as a protocol for the communication standard of the present embodiments disclosed herein.

With respect to physical wired coupling, the coupling can be by way of a dedicated coupling I/O means, such as a USB port (not shown) to provide, for example, (feedback) via the embedded software (e.g., firmware) or instructions received from the processor for programmatic control instruction.

The system 10, as shown in FIG. 1, can include a control panel, such as a graphical user interface (GUI) that enables a system operator to set configuration options and change operating parameters. In some embodiments, system 10 can also include an Internet-based configuration interface that enables remote adjustment of configuration options and operating parameters. The interface can be accessed via a web browser, for example, over a secured or insecure network connection. The Internet-based configuration interface permits remote updating of system 10 by a central computer system or another device.

As a beneficial aspect of the present application, a coupled processor (not shown) can also send, if desired, an electronic signal to a system operator to provide a warning message should a procedure, such as, for example, when an invasive medical procedure becomes perilous while using system 10, as shown in FIG. 1, as a visualization aid in the procedure. The processor can also be configured to sound an audio alarm via a speaker to alert the system operator.

Figure 11:
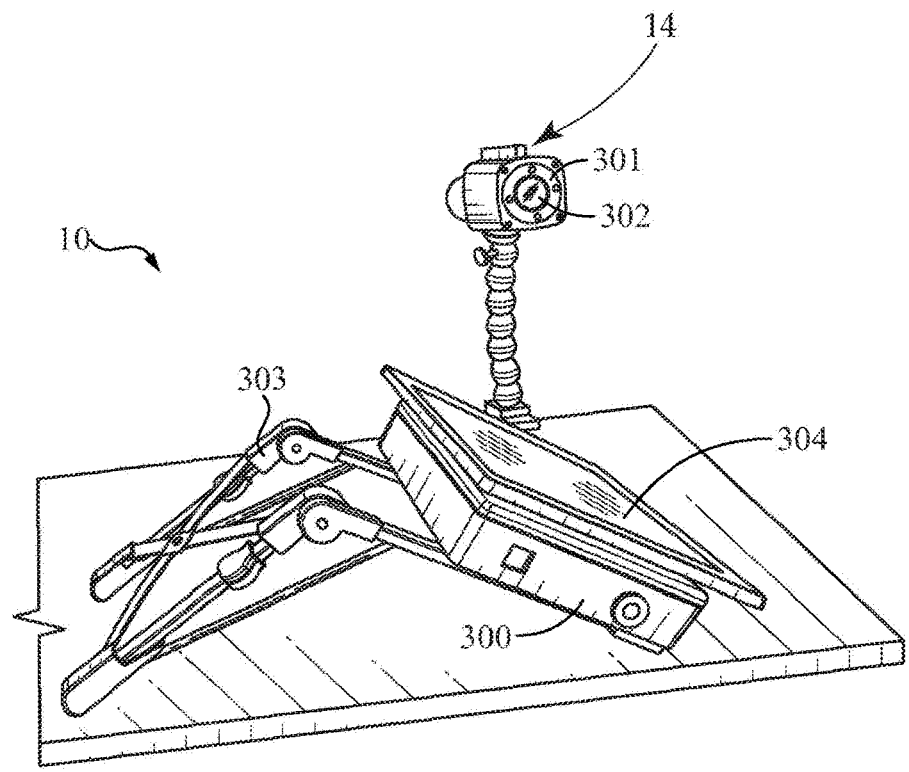
FIG. 11 illustrates the system hardware components, according to an embodiment of the present invention.

To achieve the image, at least one light source includes a plurality of Class 1 vertical cavity surface emitting lasers 301 as shown in FIG. 11. The method includes illuminating the surface of the turbid medium where light is backscattered from the surface of the turbid medium, detects a pair of complementary polarization components of the backscattered light, forms the image of the illuminated surface using the pair of complementary polarization components.

The illumination element 12 may be a plurality of lasers which are inherently polarized (e.g., linearly polarized, circularly polarized, elliptically polarized). For example, the illuminating light is linearly polarized, the pair of complementary polarization components are preferably the parallel and perpendicular components to the polarized illuminating light, and the image may be formed by subtracting the perpendicular component from the parallel component, by taking a ratio of the parallel and perpendicular components or by using some combination of a ratio and difference of the parallel and perpendicular components.

As can readily be appreciated, there are many situations in which the detection of an object present in a turbid, i.e., highly scattering, medium is highly desirable. For instance, the detection of a tumor embedded within a tissue is one such example.

One common technique for detecting tumors in tissues uses X-ray radiation. Although X-ray techniques do provide some measure of success in detecting objects located in turbid media, they are not typically well-suited for detecting very small objects, e.g., tumors less than 1 mm in size embedded in tissues, or for detecting objects in thick media. In addition, X-ray radiation can present safety hazards to a person exposed thereto. Ultrasound and magnetic resonance imaging (MRI) offer alternatives to the use of X-rays but have their own drawbacks.

Figure 12:
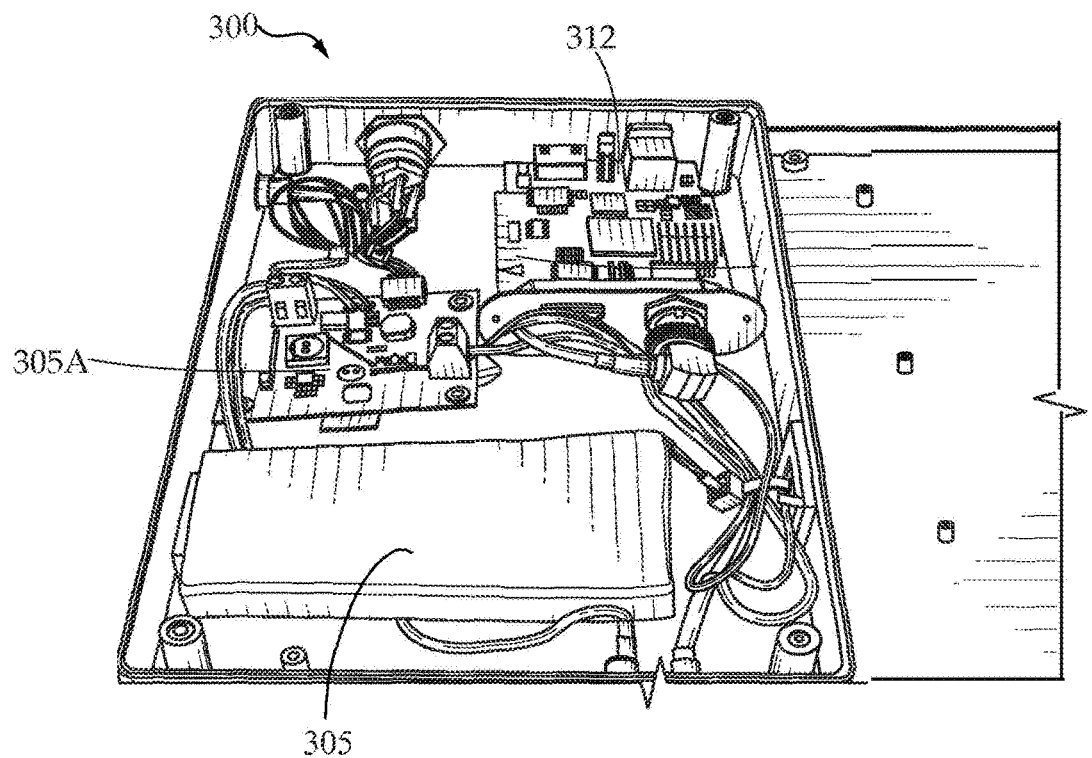
FIG. 12 illustrates the control unit, according to an embodiment of the present invention.
Figure 13:
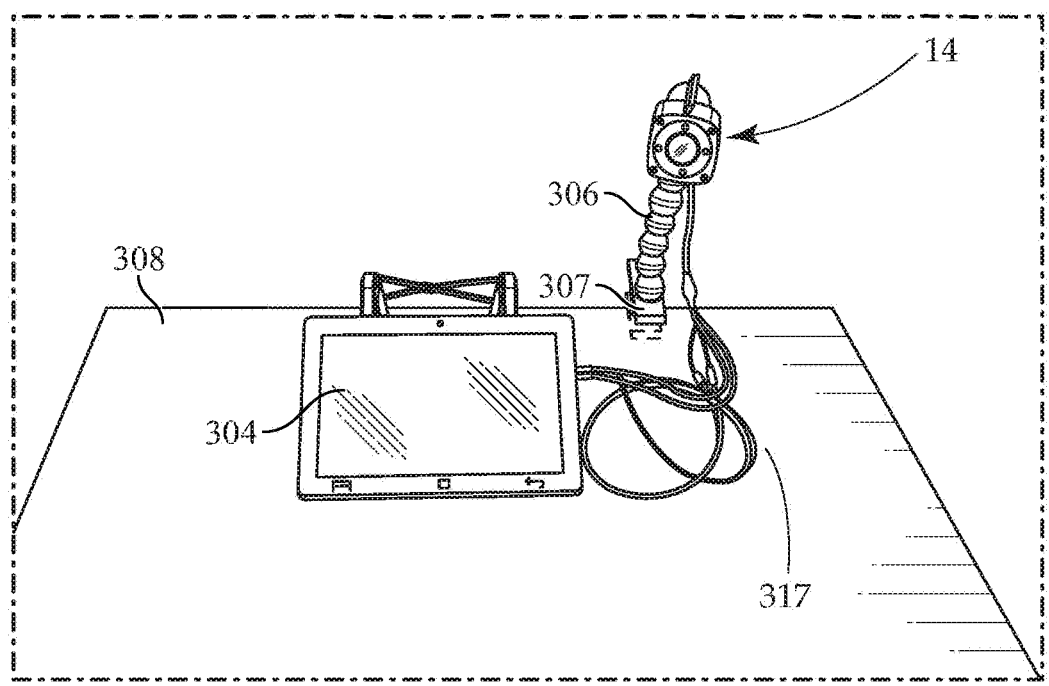
FIG. 13 illustrates the system hardware components including the image display device, according to an embodiment of the present invention.

Referring now to FIGS. 11-13, and in one embodiment, the system 10 includes a control unit 300, having at least a signal converter, power source 305, and associated electronics. In some embodiments, the associated electronics include a power management board 305A and a video capture card 312. A display device 304 connects the control unit 300 and the imaging device 14. In this embodiment, electrical power is supplied by a power source 305 within the control unit 300.

Each of the plurality of Class 1 vertical cavity surface emitting lasers 301 is positioned around a lens 302. Preferentially, the lasers 301 are positioned circumferentially equidistant around the perimeter of the lens 302.

The use of Class 1 vertical cavity surface emitting lasers 301 allow for sub-dermal structures, including veins, to be sufficiently visualized in patients who are obese or otherwise have veins that are classically difficult to visualize using the current arts. Wavelengths within the range of 700 nm and 950 nm are utilized as melanin and hemoglobin highly absorb the visible range of the light spectrum (400 nm-700 nm). Further, the use of Class 1 vertical cavity surface emitting lasers 301 permit visibility of the veins at a greater distance than the prior art. The imaging device 14 can be positioned up to six feet away from the patient while maintaining accurate imaging of the sub-dermal structures.

Once the Class 1 vertical cavity surface emitting lasers 301 reach their threshold current, the on-axis optical power is approximately 67 times greater than an LED. Drive currents can range from approximately 5 mA and 20 mA which drastically increases the apertured power while reducing the current when compared to an LED. This provides the ability to operate optical devices at greater distances at lower currents in comparison with the prior art.

In one embodiment, each Class 1 vertical cavity surface emitting laser 301 includes its own diffuser to capture the image of the entire area (e.g., an arm or hand).

For the purposes of this disclosure, a Class 1 laser can be defined as a laser safe under all conditions of normal use. This means the maximum permissible exposure cannot be exceeded when viewing a laser with the naked eye or with the aid of typical magnifying optics.

In most embodiments, the plurality of Class 1 lasers 301 include at least one vertical cavity surface emitting laser (VCSEL), which is a type of semiconductor laser diode having laser beam emission perpendicular from the top surface. This is contrary to conventional edge-emitting lasers (EEL) (also in-plane lasers), which are another type of semiconductor lasers that emit from surfaces formed by cleaving the individual chip out of the wafer. Unlike EELs or LEDs, VCSELs emit upwards or perpendicular to the top surface of the optical chip, and thus can be easily packaged as emitter arrays containing hundreds of emitters on a single chip. Other characteristics of VCSELs are their reliability, adaptability, and wavelength range. VCSELs may have a spectral or wavelength range of approximately 650 nm to 1550 nm. Other performance advantages of VCSELs as compared to either LEDs or EELs include lower power consumption, the ability to easily create 1-D and 2-D arrays of lasers on a single chip, a symmetric optical beam with a narrow beam divergence, narrow spectral width, and the compatibility with a wide variety of package types including surface mount lead frame packages and chip on board. In a preferred embodiment, the VCSELs emit light having a wavelength of approximately 850 nm.

It is an aspect of the embodiments that the system 10 is portable without the requirement of using large auxiliary appliances such as a hospital cart. In one embodiment, the imaging device 14 includes a mount 306 and fastener 307 to secure the imaging device to an object or surface such as a table 308, or, in some embodiments, to the control unit 300. To maintain portability in a clinical or home setting, the control unit 300, imaging device 14, and electronic visual display 304 can be constructed to be handheld and is sufficiently lightweight. The electronic visual display 304 can be provided as a smartphone, smart device, tablet, PDA, handheld computing system, laptop computer, handheld monitor, or similar portable electronic display.

In some embodiments, the electronic virtual display is in communication with one or more input/output (I/O) devices which can include a keyboard, mouse, feedback mechanism, auxiliary camera, an audio input device, memory, or similar I/O devices.

The power source 305 can include a power supply means which can include an AC/DC adapter. The power source 305 can include a battery, a rechargeable battery, external power source. The adapter can include means for adjusting to the power source 305 with a power output between 100V-240V.

In some embodiments, the system 10 is mounted to a hospital cart having a vertical member, a plurality of wheels, a reservoir, and an AC adapter to provide power input to the system 10.

The mount 306 and fastener 307 are provided to releasably affix the imaging device 14 to a plurality of surfaces including the control unit 300, in at least one embodiment, the display device 304, or an external surface such as a table 308, cart, or other useful regions. Further, a base assembly 303 is provided to position the system 10 on a surface. In some embodiments, a plurality of wires 317 connect the imaging device 14 to the display device 304.

Figure 14:
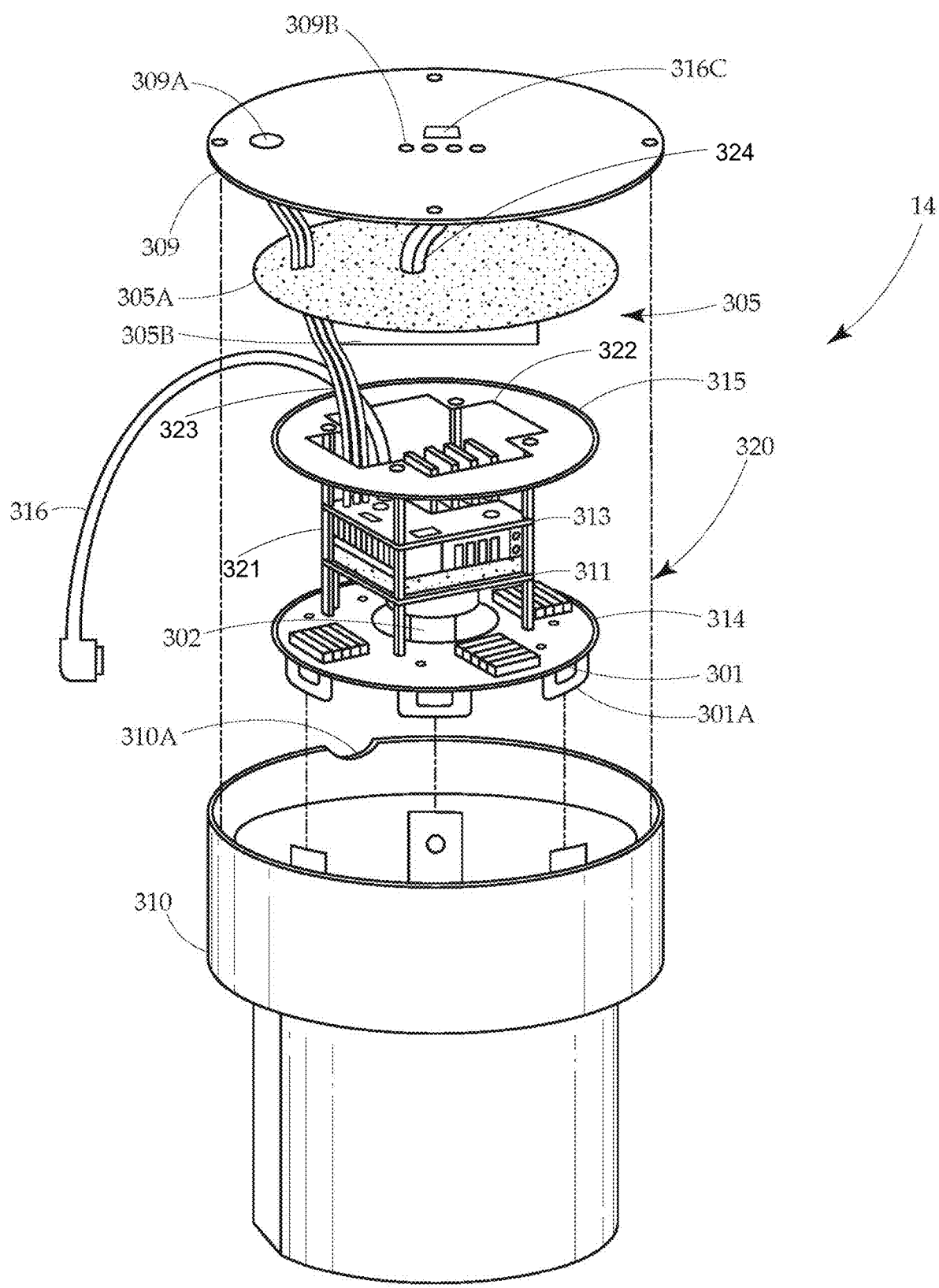
FIG. 14 illustrates a partially exploded perspective view of an embodiment of the present invention.

Turning now to FIG. 14 which shows a partially exploded perspective view of an embodiment of the imaging device 14 of the present disclosure. In contrast with other embodiments that require the imaging device 14 to be connected to a control unit 300 in order to function, in this embodiment, the imaging device 14 comprises at least the minimum necessary hardware components to function on its own in the camera lens module 320. In this embodiment, the imaging device 14 comprises an electronic housing 310 and a back cover 309. In order for the minimum necessary hardware components to be housed within the electronic housing 310, in this embodiment, the electronic housing 310 comprises a cross sectional area greater than the cross sectional area of each of the minimum necessary hardware components both individually and collectively when the hardware components are assembled to form the camera lens module 320. Accordingly, in this embodiment, the back cover 309 also comprises a cross sectional area greater than the cross section area of each of the hardware components both individually and collectively. In this embodiment, the imaging device 14 comprises a camera lens module 320, which may comprise the minimum necessary hardware components for operation of the imaging device 14.

Still referring to FIG. 14, wherein the embodiment disclosed includes at least the following hardware components assembled together in the camera lens module 320: a power source 305, a video converter board 313, a camera board 311, a lens 302, and a light board 314. In the embodiment disclosed in FIG. 14, the power source 305 comprises a battery 305B electrically connected to a power management board 305A. The back cover 309 comprises a power switch 309A, which is electrically connected to the power management board 305A, the camera board 311, and the light board 314 by wires 323, which extend through the power management board 305A. The battery 305B can be recharged by connecting an electrical I/O device to the imagine device 14. In a preferred embodiment, the I/O device used to recharge the battery 305B is a wall charger with a USB 3.0 Type C connection for charging port 316C. The back cover 309 may also comprise LED lights 309B that indicate the power levels of the battery 305B. For example, in embodiments where the back cover 309 comprises four LED lights 309B, only three of the four LED lights 309B being illuminated may mean the battery is only seventy-five percent (75%) charged. The LED lights 309B and the charging port 316C are connected to the power source 305 by wires 324.

The light board 314 comprises a plurality of Class 1 lasers 301. In the embodiment disclosed in FIG. 14, the plurality of Class 1 lasers 301 are a plurality of VCSELs, wherein the VCSELs are emitted from a semiconductor chip through a light cap 301A covering the chip. The light cap 301A may comprise at least one of an optical polarizer or optical filter. In this embodiment, each of the lasers 301 are positioned circumferentially equidistant around the perimeter of the lens 302. Light emitted from the lasers 301 may return to the imaging device 14 after bouncing off a target, and the lens 302 may capture the light as an image. In the FIG. 14 embodiment, the lens 302 is electrically connected to a camera board 311, and the camera board 311 is electrically connected to a video converter board 313. The video converter board 313 converts the live image received by the lens 302 into a signal that may be transmitted through a single wire 316. In a preferred embodiment, the single wire 316 that transmits the image is a USB wire having a USB Type A connection.

Still referring to the embodiment disclosed in FIG. 14, the electronic housing 310 defines an aperture 310A, wherein the single wire 316 passes through the aperture 310A when the back cover 309 is secured to the electronic housing 310. Additionally, in this embodiment, the camera lens module 320 comprises a support platform 315 connected to the light board 314 by four pillars 321 extending up and away from the light board 314. The video converter board 313 and the camera board 311 are in physical contact with each of the four pillars 321. The support platform 315 may have a cross sectional area less than the cross sectional area of the light board 314, and the video converter board 313 and the camera board 311 may have a cross sectional area less than the cross sectional area of the support platform 315. When the back cover 309 is secured to the electronic housing 310, the power source 305 is supported by the support platform 315 within the imaging device 14. The power management board 305A rests on the support platform 315, and the battery 305B fits within the rectangular opening 322 defined in the top of the support platform 315.

Figure 15:
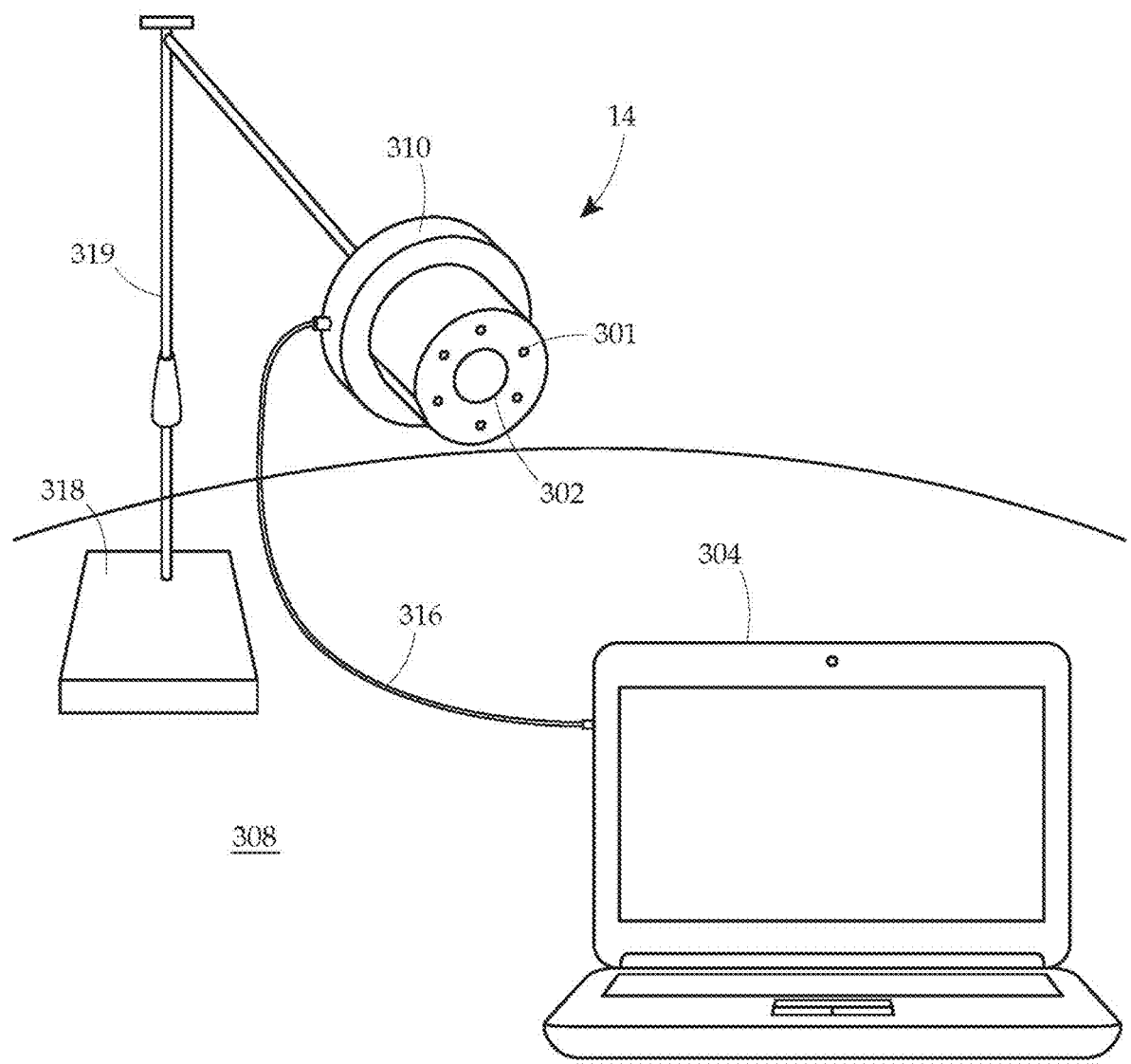
FIG. 15 illustrates a perspective view of another embodiment of the present invention.

Turning now to FIG. 15, which shows an embodiment of the imaging device 14 connected to the display device 304 by a single wire 316. In this embodiment, the system comprises a base 318 connected to at least one movable arm 319, wherein the electronic housing 310 of the imaging device 14 is rotatably connected to the movable arms 319. The rotational connection between the electronic housing 310 and the movable arms 319 allow the lasers 301, in combination with the lens 302, to image a target from multiple angles. The base 318 supports the imaging device 14 on a surface, such as a table 308.

Figure 16:
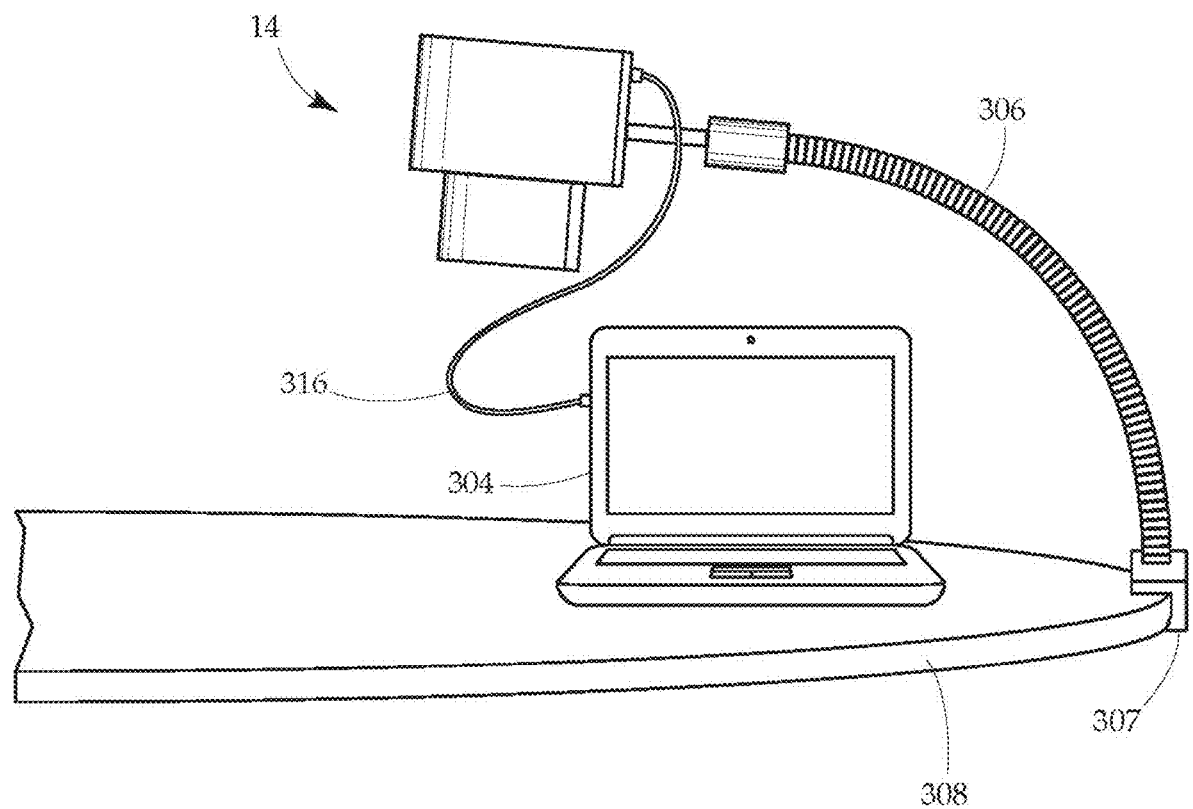
FIG. 16 illustrates another perspective view of yet another embodiment of the present invention.

FIG. 16 shows another embodiment of the imaging device 14 connected to the display device 304 by a single wire 316. In this embodiment, the imaging device 14 is rotatably connected to a mount 306, wherein the mount 306 is flexibly attached to a fastener 307. As in other embodiments, the mount 306 and fastener 307 of the present disclosure enable the imaging device 14 of the imaging system 10 to be portable, as the fastener 307 is capable of securing the imaging device 14 to a variety of surfaces, and the table 308 shown in FIG. 16 is just one example of the plethora of surfaces the fastener 307 may be secured to.

As will be appreciated by those skilled in the art, the system disclosed has a wide variety of potential uses, especially in the medical field. The following is a non-exhaustive list of the ways the system and/or method may be employed:

a) Using the imaging device 14 connected to a display device 304 to provide real-time HD video of sub-dermal veins for successful vein punctures;
b) Using the imaging device 14 connected to a display device 304 to provide real-time HD video of the pattern of the veins for non-contact vein recognition biometrics;
c) Using the imaging device 14 connected to a display device 304 to provide real-time HD video of sub-dermal tumors close to the skin;
d) Using the imaging device 14 connected to a display device 304 to provide real-time HD video of infiltration and extravasation (i.e., the inadvertent leakage of medicine from the vein into the surrounding tissue; and
e) Using the imaging device 14 connected to a display device 304 to provide real-time HD video for the detection of inflammatory breast cancer (IBC).

Many different embodiments have been disclosed herein, in connection with the above description and the drawings. It will be understood that it would be unduly repetitious and obfuscating to literally describe and illustrate every combination and sub-combination of these embodiments in addition to every potential way that the system and method may be used in practice. Accordingly, all embodiments can be combined in any way and/or combination, and the present specification, including the drawings, shall be construed to constitute a complete written description of all combinations and sub-combinations of the embodiments described herein, and of the manner and process of making and using them, and shall support claims to any such combination or sub-combination.

An equivalent substitution of two or more elements can be made for any one of the elements in the claims below or that a single element can be substituted for two or more elements in a claim. Although elements can be described above as acting in certain combinations and even initially claimed as such, it is to be expressly understood that one of more elements from a claimed combination can in some cases be excised from the combination and that the claimed combination can be directed to a sub-combination or variation of a sub-combination.

It will be appreciated by persons skilled in the art that the present embodiment is not limited to what has been particularly shown and described hereinabove. A variety of modifications and variations are possible in light of the above teachings without departing from the following claims.

What is claimed is:

1. A sub-dermal structure visualization system comprising:
an imaging device positioned to optically capture near-infrared light and relay an image, wherein the imaging device comprises a plurality of vertical cavity surface emitting lasers adapted to illuminate an area with near-infrared light and a lens positioned to optically capture the near-infrared light reflected from the area, wherein the area includes at least one sub-dermal structure within a turbid medium;

an electronic display device configured to receive and display the image relayed by the imaging device;

wherein the imaging device comprises an electronic housing containing a camera lens module and a power source, the electronic housing comprising a back cover on a top of the electronic housing;

wherein the camera lens module and the power source are arranged within the electronic housing such that the power source is positioned on top of the camera lens module;

wherein the camera lens module comprises a light board connected to a support platform by four pillars extending upward away from the light board, the light board being positioned below the support platform;

wherein the support platform comprises a cross-sectional area less than a cross-sectional area of the light board;

wherein the power source is positioned on top of the support platform and electrically connected to a power switch on the back cover;

wherein the power source comprises a battery electrically connected to a power management board;

wherein the support platform defines an opening to receive the battery, and the power management board rests on top of the support platform;

wherein the imaging device further comprises a video converter board and a camera board between the light board and the support platform;

wherein each of the video converter board and the camera board are in physical contact with each of the four pillars;

wherein each of the video converter board and the camera board have a cross-sectional area less than the cross-sectional area of the support platform;

wherein the camera board and the light board are electrically connected to the power switch by a plurality of wires extending through the power management board;

wherein the back cover comprises a plurality of light emitting diode lights and a charging port, the plurality of light emitting diode lights indicating a power level of the battery;

wherein the plurality of vertical cavity surface emitting lasers are electrically connected to a bottom of the light board; and wherein the lens is positioned in a center of the light board, the plurality of vertical cavity surface emitting lasers being positioned circumferentially around the lens; and wherein each of the plurality of vertical cavity surface emitting lasers are positioned equidistant from a perimeter of the lens.

2. The sub-dermal structure visualization system of claim 1, wherein each one of the plurality of vertical cavity surface emitting lasers comprise a diffuser.

3. The sub-dermal structure visualization system of claim 1, wherein the plurality of vertical cavity surface emitting lasers emit light comprising a spectral range of 700 nm to 950 nm.

4. The sub-dermal structure visualization system of claim 1, wherein the plurality of vertical cavity surface emitting is operated at a drive current between 10 mA and 20 mA.

5. The sub-dermal structure visualization system of claim 1, wherein the electronic housing has a cross-sectional area and the back cover is connected to the electronic housing.

6. The sub-dermal structure visualization system of claim 5, wherein the camera lens module is positioned between the electronic housing and the back cover, and the camera lens module has a cross-sectional area less than the cross-sectional area of the electronic housing.

7. The sub-dermal structure visualization system of claim 5, wherein the power source, the video converter board, the camera board, and the light board each individually have cross-sectional area less than the cross-sectional area of the electronic housing.

8. A sub-dermal structure visualization system comprising:

an imaging device positioned to optically capture near-infrared light and relay an image, wherein the imaging device comprises an electronic housing having a cross-sectional area and a back cover connected to the electronic housing, wherein the back cover comprises a power switch;

wherein the imaging device further comprises a plurality of vertical cavity surface emitting lasers adapted to illuminate an area with near-infrared light and a lens positioned to optically capture the near-infrared light reflected from the area;

wherein the area includes at least one sub-dermal structure within a turbid medium;

an electronic display device electrically connected to the imaging device and configured to receive and display the image relayed by the imaging device;

wherein the electronic housing contains a camera lens module and a power source, the camera lens module and the power source being arranged within the electronic housing such that the power source is positioned on top of the camera lens module;

wherein the camera lens module comprises a light board connected to a support platform, the light board being positioned below the support platform;

wherein the power source comprises a battery electrically connected to a power management board;

wherein the support platform defines an opening to receive the battery, and the power management board rests on top of the support platform;

wherein the imaging device further comprises a video converter board and a camera board between the light board and the support platform;

wherein each of the video converter board and the camera board have a cross-sectional area less than the cross-sectional area of the support platform;

wherein the camera board and the light board are electrically connected to the power switch by a plurality of wires extending through the power management board;

wherein the power management board is electrically connected to the power switch on the back cover;

wherein the back cover comprises a plurality of light emitting diode lights and a charging port, the plurality of light emitting diode lights indicating a power level of the battery;

wherein the plurality of light emitting diode light and the charging port are connected to the power management board by a different plurality of wires than the camera board and the light board; and wherein the plurality of vertical cavity surface emitting lasers are electrically connected to a bottom of the light board.

9. The sub-dermal structure visualization system of claim 8, wherein the imaging device further comprises a single wire, and the electronic housing defines an aperture, wherein the single wire extends through the aperture of the electronic housing and electrically connects the imaging device to the electronic display device.

10. The sub-dermal structure visualization system of claim 8, wherein the plurality of vertical cavity surface emitting lasers are positioned circumferentially around the lens.

11. The sub-dermal structure visualization system of claim 8 further comprising a base and at least one connecting arm, wherein the base is connected to the connecting arm, and a movable arm is rotatably attached to the imaging device.

12. The sub-dermal structure visualization system of claim 8 further comprising a mount and a fastener, wherein the fastener is connected to the mount, and the mount is rotatably attached to the imaging device, wherein the mount and the fastener releasably affix the imaging device to a surface.

13. The sub-dermal structure visualization system of claim 8, wherein the vertical cavity surface emitting lasers are covered by a light cap, wherein the light cap comprises at least one of an optical polarizer or an optical filter.

14. The sub-dermal structure visualization system of claim 8, wherein the at least one sub-dermal structure within the turbid medium comprises a vein and a plurality of hemoglobin molecules.

15. The sub-dermal structure visualization system of claim 8, wherein the battery supplies electrical power to the imaging device, the camera board is electrically connected to the lens, and the video converter board is electrically connected to the camera board.

16. The sub-dermal structure visualization system of claim 15, wherein the power management board, the battery, the video converter board, the camera board, and the light board are housed within the electronic housing, and each comprise a cross-sectional area less than the cross-sectional area of the electronic housing.

17. The sub-dermal structure visualization system of claim 15, wherein the camera board is configured to receive an optical signal from the lens, and the video converter board is configured to convert the optical signal into a visualization signal that is relayed to the electronic display device through a single wire electrically connected to the video converter board.

18. The sub-dermal structure visualization system of claim 17, wherein the electronic display device utilizes image enhancement software configured to select for a range of intensities from the visualization signal and display the image.

* * * * *